(12) United States Patent
Diamond et al.

(10) Patent No.: US 7,771,583 B2
(45) Date of Patent: Aug. 10, 2010

(54) ELECTROCHEMICAL DETERMINATION OF ANALYTES

(75) Inventors: Steven Diamond, Somerville, MA (US); Ian Harding, Somerville, MA (US); Sridhar Iyengar, Salem, NH (US); Richard Williams, Andover, MA (US)

(73) Assignee: Agamatrix, Inc., Salem, NH (US)

( * ) Notice: Subject to any disclaimer, the term of this patent is extended or adjusted under 35 U.S.C. 154(b) by 300 days.

(21) Appl. No.: 11/874,772

(22) Filed: Oct. 18, 2007

(65) Prior Publication Data

US 2008/0093230 A1     Apr. 24, 2008

Related U.S. Application Data

(60) Provisional application No. 60/862,016, filed on Oct. 18, 2006, provisional application No. 60/862,002, filed on Oct. 18, 2006.

(51) Int. Cl.
*G01N 33/66* (2006.01)
*G01N 27/26* (2006.01)

(52) U.S. Cl. .................. 205/792; 205/775; 205/779; 204/401

(58) Field of Classification Search ................. 204/400, 204/402, 403, 401; 205/792, 775, 779, 782, 205/775.5
See application file for complete search history.

(56) References Cited

U.S. PATENT DOCUMENTS

| | | | |
|---|---|---|---|
| 4,798,655 A * | 1/1989 | Diamond | .................. 205/775 |
| 5,243,516 A | 9/1993 | White | |
| 5,352,351 A | 10/1994 | White et al. | |
| 5,942,102 A | 8/1999 | Hodges et al. | |
| 6,144,869 A | 11/2000 | Berner et al. | |
| 6,251,260 B1 * | 6/2001 | Heller et al. | .................. 205/777.5 |
| 6,284,125 B1 | 9/2001 | Hodges et al. | |
| 6,365,033 B1 | 4/2002 | Graham et al. | |
| 6,885,883 B2 | 4/2005 | Parris et al. | |
| 6,990,422 B2 | 1/2006 | Laletin et al. | |
| 2002/0130674 A1 | 9/2002 | Lagowski et al. | |
| 2005/0279631 A1 | 12/2005 | Celentano | |
| 2005/0284758 A1 | 12/2005 | Funke et al. | |
| 2006/0231418 A1 * | 10/2006 | Harding et al. | .................. 205/775 |
| 2006/0231423 A1 * | 10/2006 | Harding et al. | .................. 205/792 |
| 2006/0231424 A1 | 10/2006 | Harding et al. | |
| 2006/0231425 A1 * | 10/2006 | Harding et al. | .................. 205/792 |

OTHER PUBLICATIONS

Matsumoto, et al., "Fundamental Studies of Glucose Oxidase Deposition on a Pt Electrode", Analytical Chemistry, Jan. 15, 2002, pp. 362-367, vol. 74, No. 2.

* cited by examiner

*Primary Examiner*—Alexa D Neckel
*Assistant Examiner*—Jennifer Dieterle
(74) *Attorney, Agent, or Firm*—Larson & Anderson, LLC

(57) ABSTRACT

Determination of an analyte with increased accuracy is achieved by electrochemically determining an initial analyte concentration, performing a plurality of amperometric/potentiometric switching cycles, observing a characteristic of the signal during each of the plurality of switching cycles, determining an averaged value for the characteristic of the signal, and correcting the initial measurement value to arrive at a final measurement value of analyte concentration or rejecting the initial measurement value depending on the averaged value of the characteristic of the signal. The characteristic of the signal that is observed is not per se indicative of the amount of analyte present in a sample. Rather, it is a characteristic of the signal that reflects the quality of the electrodes, the extent of fill of the electrochemical cell or characteristics of the sample other than analyte concentration such as oxygen levels or hematocrit.

21 Claims, 3 Drawing Sheets ately for the needs of measuring analytes such as glucose in very small volumes of
ELECTROCHEMICAL DETERMINATION OF ANALYTES

STATEMENT OF RELATED APPLICATIONS

This application claims the benefit of U.S. Provisional Application Nos. 60/862,016, filed Oct. 18, 2006, and 60/862,002 filed Oct. 18, 2006. Ser. No. 60/862,016 is incorporated herein by reference in its entirety.

BACKGROUND

This application relates to the electrochemical determination of analytes such as glucose.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

In some assay formats, electrochemical detection of glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produce a reduced mediator. Reduced mediator is oxidized at one of the electrodes, and then diffuses back to either be reduced at the other electrode or by the reduced enzyme to complete the cycle, and to result in a measurable current. The measured current is related to the amount of glucose in the sample, and various techniques are known for determining glucose concentrations in such a system. (See, U.S. Pat. Nos. 6,284,125; 5,942,102; 5,352,2,351; and 5,243,516, which are incorporated herein by reference.)

Notwithstanding developments in the art, there is a continuing need to improve the accuracy of test systems for measuring analytes such as glucose in very small volumes of blood.

SUMMARY OF THE INVENTION

The present invention provides a method for determination of an analyte with increased accuracy comprising the steps of:
  (a) electrochemically determining an initial measurement value of analyte concentration in a liquid sample disposed between a working and a counter electrode,
  (b) performing a plurality of amperometric/potentiometric switching cycles between the working and counter electrodes,
  (c) observing a characteristic of the signal during each of the plurality of switching cycles,
  (d) determining an averaged value for the characteristic of the signal, and
  (e) correcting the initial measurement value to arrive at a final measurement value of analyte concentration or rejecting the initial measurement value depending on the averaged value of the characteristic of the signal.

The initial determination of analyte concentration may be made before, during or after the plurality of amperometric/potentiometric switching cycles.

DETAILED DESCRIPTION OF THE INVENTION

I. Definitions

Figure 1:
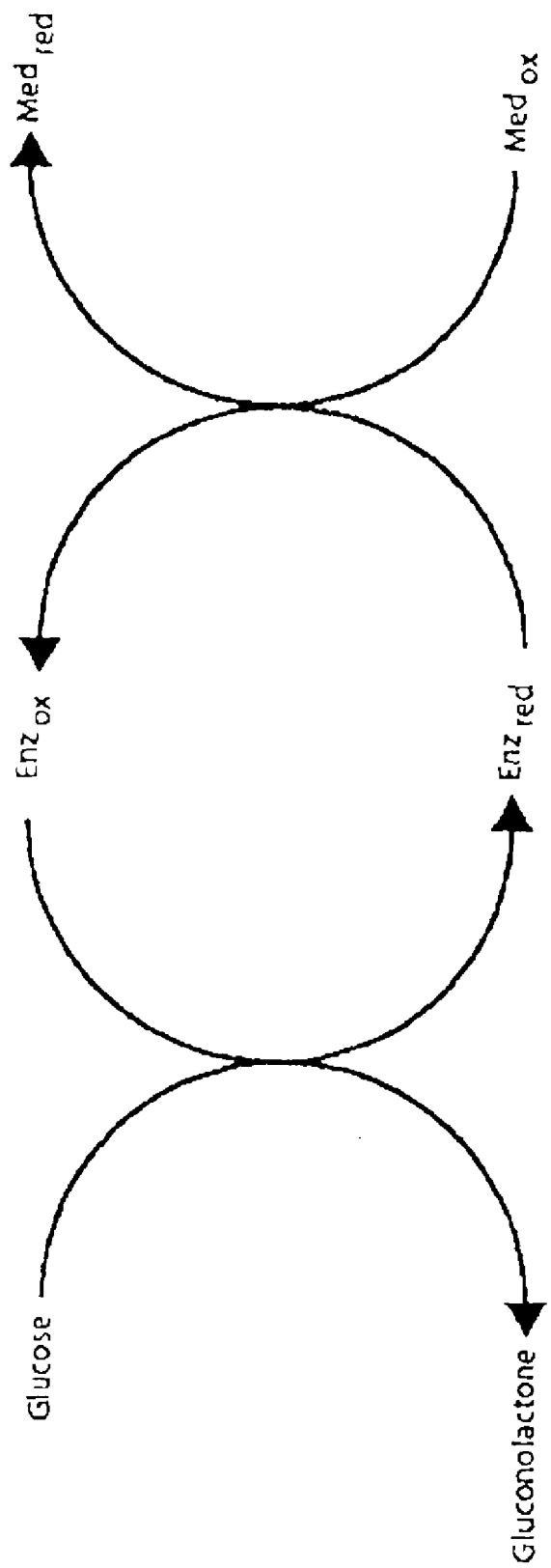
FIG. 1 shows the election transfer reactions that occur in a conventional amperometric glucose detector.

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment.

(b) "averaged value" encompasses simple numerical averages in which all data points are included, and weighted averages in which outliers are omitted, or included with reduced weight.

(c) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(d) "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

(e) "facing electrodes" are a pair of electrodes disposed parallel to but in a separate plane from each other. Some or all of the opposed surfaces of a pair of facing electrodes overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes.

(f) "predetermined amount" is used in this application to refer to amounts that are determined empirically for a particular meter or test strip or meter/strip combination. The predetermined amounts will reflect an optimization for the needs of the user, taking into account the confidence levels needed, and need not achieve the best possible results or 100% accuracy.

(g) "switching off" of the applied potential refers to the creation of an open circuit that forces the current to be zero (by opening a switch or introducing a high impedance into the circuit) that allows a built-up chemical concentration gradient and ion adsorption in the double layer to determine the potential between the electrodes. This is not the same thing as setting the voltage to zero volts.

(h) "series electrode resistance" causes a difference between the applied voltage, and the actual voltage perceived by the electrochemistry at the electrode. Electrode resistance arises as a result of the resistance of the electrode material and the connectors associated with the electrodes, fouling of the electrode and similar factors.

(i) $V_{drop}$ is the difference between the applied voltage and the actual voltage at the electrode that arises as a result of series electrode resistance. $V_{drop-avg}$ is a numerical average of a plurality of measured $Vd_{drop}$ values determined in a plurality of switching cycles.

(j) "mediator" refers to a chemical species that is electrochemically detected. Numerous electron transfer mediators suitable for detection of analytes such as glucose are known, and include without limitation iron, ruthenium, and osmium C compounds. In some embodiments of the invention, the mediator is produced through one or more reaction steps and is related to the concentration of the actual analyte, such as glucose. The present invention is also applicable, however, to circumstances in which the detected chemical species is the reduced form of the analyte to be detected, and this is also an embodiment of the invention.

(k) "$I_{pre-switch}$" refers to a current value determined prior to the switching off of the applied potential. The time at which this current measurement is taken is sufficiently close in time to the time $t_{switch}$ that it is representative of current at the actual time of the switching. As will be apparent, the amount of time that the current measurement can be made prior to $t_{switch}$ is dependent on the rate of change of the current at this time, with longer times being acceptable if the switch is made in the plateau region, and shorter times being required when the value of current is rapidly changing.

Numerical values in the specification and claims of this application should be understood to include numerical values which are the same when reduced to the same number of significant figures and numerical values which differ from the stated value by less than the experimental error of the technique used to measure the value.

II. The Invention

The present application describes a method and apparatus for the determination of an analyte such as glucose in a liquid sample that makes use of a plurality of alternating amperometric and potentiometric cycles to observe a characteristic of the signal. The use of a plurality of switching cycles in the method of the invention results in improved accuracy since the significance of anomalous readings is reduced by averaging. On the other hand, each cycle takes time, especially if a given device requires time for the current to settle after re-application of the potential, and therefore increases the amount of time it takes to achieve a result for display to a user. The number of cycles used is therefore a compromise between these two factors. In general, suitable numbers of cycles are less than 10 cycles, for example 2, 3, 4 or 5. The number of cycles may also be determined dynamically based on the observed variance in the switching cycles already evaluated. Thus, if the first two or three cycles produce essentially the same value for the observed characteristics it may be dynamically determined that this is a sufficient number of cycles.

The characteristic of the signal that is observed is not per se indicative of the amount of analyte present in a sample (although it may contain information about the amount of analyte which could, using different procedures be utilized). Rather, it is a characteristic of the signal that reflects the quality of the electrodes, the extent of fill of the electrochemical cell or characteristics of the sample other than analyte concentration (such as hematocrit). Depending on the characteristic of the signal observed, various issues encountered in electrochemical analysis can be addressed using this method. Specific characteristics that can be observed during the cyclic process include various measures of the resistance of the electrodes (an indicator of fouling or damaged electrodes); double layer capacitance as a measure of partial fill of the electrochemical cell, and mobility factors that reflect mediator mobility and also side reactions dependent on oxygen levels in a sample.

Series Electrode Resistance

"Series electrode resistance" causes a difference between the applied voltage, and the actual voltage perceived by the electrochemistry at the electrode. Electrode resistance arises as a result of the resistance of the electrode material and the connector s associated with the electrodes, fouling of the electrode and similar factors. U.S. patent application Ser. No. 10/907,817 filed Apr. 15, 2005, now US Patent Publication No. US 2006-0231424 (which application is incorporated herein by reference in its entirety) discloses a method for correcting for variations in the series electrode resistance of electrodes during the determination of an analyte. In this method, after sufficient information is collected to make a determination of analyte, the applied potential is switched off at time $t_{switch}$, thus making a change from an amperometric mode (applied potential observed current) to a potentiometric mode (observed potential). At this point in time, there remains a potential difference between the electrodes as a result of a chemical potential gradient. In the absence of resistance, this potential would decay with a time constant determined by the mobility of the mediator in the system. However, when the actual voltage profile of an electrochemical strip with carbon electrodes or other Sources of resistance is measured, an immediate drop in voltage is observed after the applied potential is switched off. The magnitude of this drop, $V_{drop}$ is a function of several factors, including the resistance of the electrode material and the connectors associated with the electrodes, fouling of the electrode and similar factors. Thus, the drop is larger with carbon electrodes than with a low resistance electrode such as one made of gold, but may still be present regardless of the electrode material of other sources of series resistance are present.

In some embodiments of the present invention, $V_{drop}$ is determined in plurality switching cycles, each switching cycle comprising the steps of switching off the applied potential at time $t_{switch}$ and determining the magnitude, $V_{drop}$, of the immediate voltage drop, and then switching the potential back on to prepare for the next switching cycle. As will be apparent in the final switching cycle, the potential need not be switched back on. Thus, the device operates ill an alternate series of amperometric and potentiometric modes (amp-> pot->amp->pot . . . ). The measured values of $V_{drop}$ for each cycle are averaged to produce a value $V_{drop-avg}$ which can either be used directly for comparison or used in a calculation of track resistance as discussed below. Stated numerically, for n switching cycles $V_{drop-avg}$ is given by the equation:

$$\frac{1}{n}\left(\sum_n V_{drop,n}\right) = V_{drop-avg}$$

Error Detection Using $V_{drop-avg}$

In order to detect errors, the determined magnitude of $V_{drop-avg}$ is checked against a predetermined range, and the test is rejected if the magnitude of $V_{drop-avg}$ falls outside of the range. In some embodiment of the invention, the predetermined range is open-ended at on end, and thus is equivalent to a single threshold value. In other embodiments of the invention, the predetermined range has both an upper and a lower bound.

In order to determine appropriate values for the bounds of the predetermined range, a plurality of test strips are tested under conditions that are assumed to exclude error states. These measurements determine the range of normal values that are likely to be encountered. A second set of experiments is then performed in test strips in which errors are intentionally introduced. For example, test trips can be intentionally damaged, for example by scratching the electrode surface; intentionally fouled; the connectors can be intentionally dirtied to create strips that should have higher than normal series electrode resistance, and thus higher values of $V_{drop}$. Finally, a set of experiments that are expected to produce low levels of $V_{drop-avg}$, for example experiments with shorted electrodes, are performed. The values for $V_{drop-avg}$ for each of these sets of experiments are plotted, along a line, and a confidence range or threshold is defined in which most, if not all, of the non-error measurements and substantially none of the error measurements are included within the range. FIG. 4B of US 2006/0231424 shows one set of data determined in this way for single measurements of $V_{drop}$.

Error Determination Using $R_{track}$

As an alternative to detection of errors using $V_{drop}$ or $V_{drop-avg}$ directly, the potential difference can be maintained for a period of time sufficient to determine a current, $I_{pre-switch}$ prior to switching off the application potential or initiation of the switching cycles. The determined value of $I_{pre-switch}$ may be used to calculate track resistance, $R_{track}$ according to the formula $R_{track}=V_{drop}/I_{pre-switch}$ when only a single value of $V_{drop}$ is determined. Alternatively, when n switching cycles are performed, $R_{track}$ is given by the formula:

$$R_{track} = \frac{1}{n}\left(\sum_n V_{drop,n}/I_{pre-switch,n}\right), \text{ or}$$

$$R_{track} = \left(\frac{\sum_n V_{drop,n}}{\sum_n I_{pre-switch,n}}\right).$$

Medians and averages omitting outliers may also be used rather than arithmetic averages of all values. The determined value of $R_{track}$ is then compared to a predetermined range (which may be open-ended) and the reading is rejected if the value falls outside the range.

Use of $R_{track}$ rather than $V_{drop}$ or $V_{drop-avg}$ can give superior results, particularly in instances where the measured levels of analyte, and thus the magnitude of the voltage signal and the plateau current can be variable, since it tends to normalize the sample based effects on $V_{drop}$ or $V_{drop-avg}$ and make the correction process more robust.

Figure 2A:
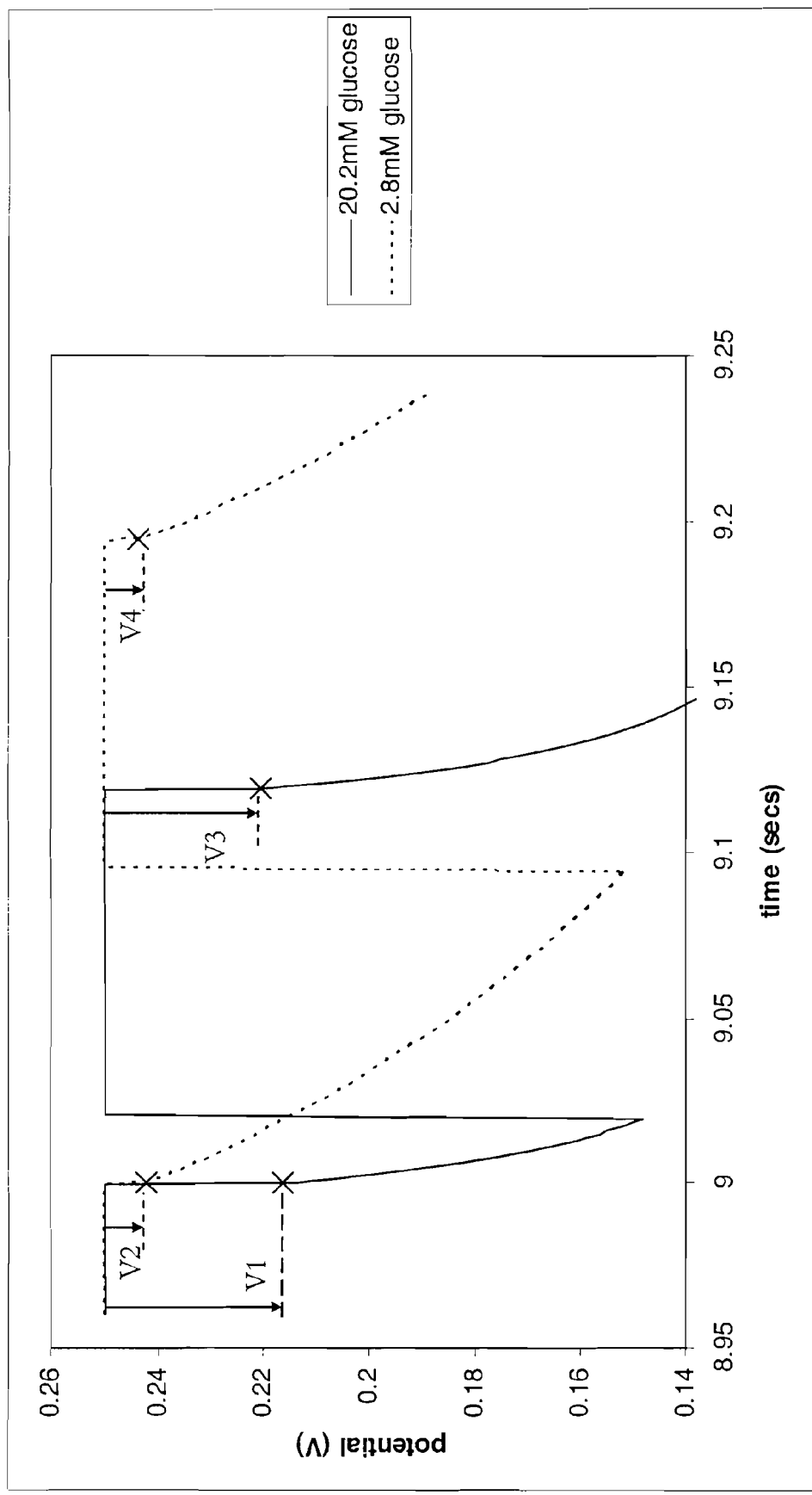
FIGS. 2A and 2B show potential versus time and current versus time in an example with 2 switching cycles for 2.8 mM and 20.2 mM glucose standards.
Figure 2B:
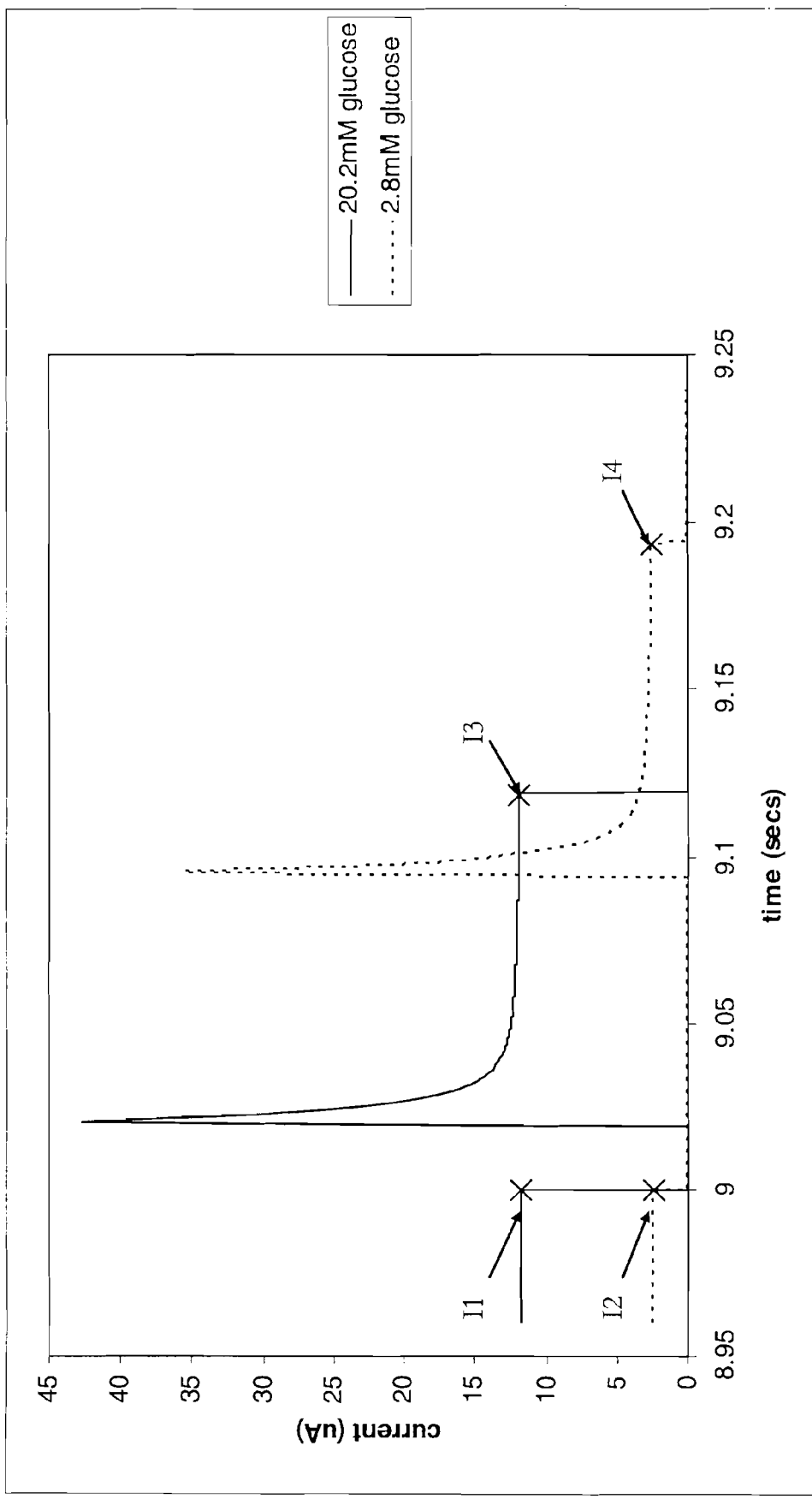

FIGS. 2A and 2B show potential versus time and current versus time in an example with 2 switching cycles for 2.8 mM and 20.2 mM glucose standards. Both figures begin at 8.95 seconds after first application of the potential difference, when the current I1, I2 is in the plateau region and the potential is switched on. At 9 seconds, the current is switched off, and the immediate drop in potential and current is observed. In the case of the 20.2 mM glucose (solid line) a large $V_{drop}$=V1 is observed followed by further decay of the potential over time. Thereafter, at approximately 9.02 seconds, the potential is reapplied, which results in a spike in the current followed by a decay to a plateau value. At about 9.12 seconds this potential is turned off, resulting in the second value for $V_{drop}$=V3. The sample with 2.8 mM glucose is handled ill substantially the same way. The time intervals shown in the figures are longer for this sample but they could be the same. Specifically, the switching on of potential in the case of the 2.8 mM sample occurs at about 9.09 seconds and the switching off of the potential occurs at about 9.19 seconds.

Partial Fill

Failure to completely fill an electrochemical cell can also result in error which requires the correction or rejection of an initial analyte determination. U.S. patent application Ser. No. 10/907,813, filed Apr. 15, 2005, now US Patent Publication No. US 2006-0231418 (which application is incorporated herein by reference in its entirety) discloses a method for detecting partial fill in which a potential difference is applied between the electrodes of a test strip, and then switched off. Observation of current generated is used to determine a double layer charging or discharging between the electrodes. Voltage change after the applied potential is switched off is used in combination with the double layer charging or discharging to determine double layer capacitance of test strip. The determined double layer capacitance is compared to a reference value, wherein a double layer capacitance less than the reference value is an indication that the liquid sample covers a portion of the facing electrodes and that the electrochemical test strip is only partially filled. Based on this comparison, a correction can be made to the final analyte determination (if the difference is small) or the test can be rejected because of incomplete filling.

In accordance with the present invention, a plurality of amperometric/potentiometric switching cycles are performed so that a plurality of values for double layer capacitance arc obtained. An average of these numbers (mean, median, mean n minus outliers) is used rather than an individual number in determining whether to make corrections or to reject the test.

By way of non-limiting example, the following sequence may be followed to determine an average discharge capacitance:

(a) apply potential, measure a first current value current
(b) switch off potential, observe decay of potential,
(c) determine first double layer capacitance from current and observation from potential decay;
(d) reapply potential, optionally observe a second . . . n a current value
(e) switch off potential, observe decay of potential,
(f) determine second . . . n double layer capacitance from first or second . . . n current and second . . . n observation from potential decay;
(g) determine average value of double layer capacitance and compare to reference value.

In the case of a charging capacitance, the observation of potential is made when the potential is applied to the electrodes. Thus, the use of multiple switching cycles in this case requires an observation of the charging process during at least two applications of potential, with intervening switching off of the potential.

In either discharge or charging measurements, the double layer capacitance may be an integral or differential determination of capacitance.

It is also observed in Ser. No. 10/907,813, filed Apr. 15, 2005 (US 2006-0231418) that an observed $V_{drop}$ can be used as a modifier of the parameters used in the determination of capacitance. As noted above, the plurality of cycles can be used to determine an average $V_{drop}$, and this $V_{drop-avg}$ can be used as a correction factor in place of $V_{drop}$ as previously described.

Mobility Measurements

U.S. patent application Ser. No. 10/907,813, filed Apr. 15, 2005 (US 2006-0231418) and U.S. patent applications Ser. Nos. 10/907,803 and 10/907,818 filed Apr. 15, 2006 and now published as US Patent Publications US 2006-0231423 and US 2006-0231425, respectively, (both of which are incorporated herein by reference in their entirety) describe determination of a parameter referred to as $t_{mob}$. "$t_{mob}$" is a time determined experimentally during an analysis that reflects the mobility of mediator in a particular sample in a particular test cell. $t_{mob}$ is the time after the applied potential is switched off that it takes for the potential between the electrodes to decay to a pre-determined value. An additive correction factor is then determined as a function of $t_{mob}$ and the temperature of the sample, and used to correct the raw analyte reading for oxygen in the sample, for determination of hematocrit, and for distinguishing between a blood sample and a control solution applied to an electrochemical test strip. $t_{mob}$ can also be used to detect abnormal traces which can lead to the rejection of a test.

In accordance with the present invention, a plurality of values for $t_{mob}$ are determined in a plurality of switching cycles and an average value for $t_{mob}$ is determined from these individual values (mean, median, mean excluding outliers). This average value is used in the same manner as previously disclosed for the single value of $t_{mob}$ to correct or reject an assay result.

What is claimed is:

1. A method for determination of an analyte with increased accuracy comprising the steps of:
  (a) electrochemically determining an initial measurement value of analyte concentration in a liquid sample disposed between a working and a counter electrode,
  (b) performing a plurality of amperometric/potentiometric switching cycles between the working and counter electrodes,
  (c) observing a characteristic of the signal during each of the plurality of switching cycles,
  (d) determining an averaged value for the characteristic of the signal, and
  (e) correcting the initial measurement value to arrive at a final measurement value of analyte concentration or rejecting the initial measurement value depending on the averaged value of the characteristic of the signal.

2. The method of claim 1, wherein the characteristic of the signal that is observed reflects the quality of the electrodes, the extent of fill of the electrochemical cell or a characteristic of the sample other than analyte concentration.

3. The method of claim 2, wherein the characteristic of the signal that is observed is series electrode resistance as an indication of the quality of the electrodes.

4. The method of claim 3, wherein each switching cycle comprising the steps of switching off the applied potential at time $t_{switch}$ and determining the magnitude, $V_{drop}$, of the immediate voltage drop occurring after $t_{switch}$, and then switching the potential back on to prepare for the next switching cycle, and wherein the averaged value of $V_{drop}$ is determined according to equation:

$$\frac{1}{n}\left(\sum_n V_{drop,n}\right) = V_{drop-avg},$$

where n is the number of switching cycles.

5. The method of claim 3, wherein each switching cycle comprising the steps of switching off the applied potential at time $t_{switch}$ and determining the magnitude, $V_{drop}$, of the immediate voltage drop occurring after $t_{switch}$, and then switching the potential back on to prepare for the next switching cycle, and determining a current, $I_{pre-switch}$ prior to switching off the application potential or initiation of the switching cycles, and then determining an average value of track resistance according to the equation:

$$R_{track} = \frac{1}{n}\left(\sum_n V_{drop,n} / I_{pre-switch,n}\right), \text{ or}$$

$$R_{track} = \left(\frac{\sum_n V_{drop,n}}{\sum_n I_{pre-switch,n}}\right),$$

wherein n is the number of switching cycles.

6. The method of claim 5, wherein $I_{pre-switch}$ is a plateau current.

7. The method of claim 2, wherein the characteristic of the signal that is observed is double-layer capacitance as an indication of the extent of fill of the electrochemical cell.

8. The method of claim 7, wherein the plurality of switching cycles include the steps of:
  (i) applying a potential and measuring a first current value,
  (ii) switching off the potential and observing a first decay of potential,
  (iii) determining a first double layer capacitance from the first current value and the observed first potential decay,
  (iv) reapplying a potential to observe a second to the nth current value,
  (v) switching off the potential and observing a second to the nth decay of potential,
  (vi) determining a second to the nth double layer capacitance from the first or second to the nth current and the second to the nth observation of potential decay, and
  (vi) determining an average value of double layer capacitance.

9. The method of claim 7, wherein the plurality of switching cycles include the steps of:
  (i) applying a potential and measuring a first current value,
  (ii) switching off the potential and observing a first decay of potential,
  (iii) reapplying a potential to observe a first charging current transient and determining a first double layer capacitance from the first charging current transient and the first potential decay,
  (iv) switching off the potential and observing a second to the nth decay of potential, and then reapplying the potential to observe a second to the nth charging current transient and determining a second to the nth double layer capacitance from the second to the nth charging current transient and the second to the nth potential decay, and
  (v) determining an average value of double layer capacitance.

10. The method of claim 2, wherein the characteristic of the signal that is observed reflects a characteristic of the sample other than analyte concentration which reflects oxygen levels in the sample.

11. The method of claim 1, wherein the initial determination of analyte concentration is made before the plurality of amperometric/potentiometric switching cycles.

12. The method of claim 11, wherein the characteristic of the signal that is observed reflects the quality of the electrodes, the extent of fill of the electrochemical call or a characteristic of the sample other than analyte concentration.

13. The method of claim 12, wherein the characteristic of the signal that is observed is series electrode resistance as an indication of the quality of the electrodes.

14. The method of claim 13, wherein each switching cycle comprising the steps of switching off the applied potential at time $t_{switch}$ and determining the magnitude, $V_{drop}$, of the immediate voltage drop occurring after $t_{switch}$, and then switching the potential back on to prepare for the next switching cycle, and wherein the averaged value of $V_{drop}$ is determined according to equation:

$$\frac{1}{n}\left(\sum_n V_{drop,n}\right) = V_{drop\text{-}avg},$$

where n is the number of switching cycles.

15. The method of claim 13, wherein each switching cycle comprising the steps of switching off the applied potential at time $t_{switch}$ and determining the magnitude, $V_{drop}$, of the immediate voltage drop occurring after $t_{switch}$, and then switching the potential back on to prepare for the next switching cycle, and determining a current, $I_{pre\text{-}switch}$ prior to switching off the application potential or initiation of the switching cycles, and then determining an average value of track resistance according to the equation:

$$R_{track} = \frac{1}{n}\left(\sum_n V_{drop,n} / I_{pre\text{-}switch,n}\right), \text{ or}$$

$$R_{track} = \left(\frac{\sum_n V_{drop,n}}{\sum_n I_{pre\text{-}switch,n}}\right),$$

wherein n is the number of switching cycles.

16. The method of claim 15, wherein $I_{pre\text{-}switch}$ is a plateau current.

17. The method of claim 12, wherein the characteristic of the signal that is observed is double-layer capacitance as an indication of the extent of fill of the electrochemical cell.

18. The method of claim 17, wherein the plurality of switching cycles include the steps of:
   (i) applying a potential and measuring a first current value,
   (ii) switching off the potential and observing a first decay of potential,
   (iii) determining a first double layer capacitance from the first current value and the observed first potential decay,
   (iv) reapplying a potential to observe a second to the nth current value,
   (v) switching off the potential and observing a second to the nth decay of potential,
   (vi) determining a second to the nth double layer capacitance from the first or second to the nth current and the second to the nth observation of potential decay, and
   (vi) determining an average value of double layer capacitance.

19. The method of claim 17, wherein the plurality of switching cycles include the steps of:
   (i) applying a potential and measuring a first current value,
   (ii) switching off the potential and observing a first decay of potential,
   (iii) reapplying the potential to observe a first charging current transient and determining a first double layer capacitance from the first charging current transient and the first potential decay,
   (iv) switching off the potential and observing a second to the nth decay of potential, and then reapplying the potential to observe a second to the nth charging current transient and determining a second to the nth double layer capacitance from the second to the nth charging current transient and the second to the nth potential decay, and
   (v) determining an average value of double layer capacitance.

20. The method of claim 2, wherein the characteristic of the signal that is observed reflects a characteristic of the sample other than analyte concentration which reflects hematocrit in the sample.

21. The method of claim 1, in which the averaged value is a weighted average.

* * * * *